United States Patent
Schefczik

Patent Number: 4,667,051
Date of Patent: May 19, 1987

[54] PREPARATION OF CYANO-SUBSTITUTED ENOL ETHERS

[75] Inventor: Ernst Schefczik, Ludwigshafen, Fed. Rep. of Germany

[73] Assignee: BASF Aktiengesellschaft, Ludwigshafen, Fed. Rep. of Germany

[21] Appl. No.: 866,920

[22] Filed: May 27, 1986

[30] Foreign Application Priority Data

May 31, 1985 [DE] Fed. Rep. of Germany ....... 3519456

[51] Int. Cl.$^4$ .................. C07C 121/34; C07C 121/75
[52] U.S. Cl. .................................. 558/375; 548/330;
558/409; 558/439; 558/449
[58] Field of Search ............... 558/375, 409, 439, 449;
548/330

[56] References Cited

PUBLICATIONS

Junek et al, Monatsh. Chem., 108, 895 (1977).

Primary Examiner—Dolph H. Torrence
Attorney, Agent, or Firm—Oblon, Fisher, Spivak, McClelland & Maier

[57] ABSTRACT

Compounds of the formula I

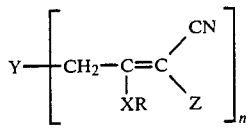

where R is alkyl of 1 to 10, preferably 1 to 4, carbon atoms, X is O or S, Y is hydrogen or nitrophenyl which is unsubstituted or substituted by chlorine, bromine, methoxy or methyl, when n is 1, and is $C_2$–$C_6$-alkylene when n is 2, and Z is cyano or 2-benzimidazolyl, are prepared by a process in which an iminoether of the formula II

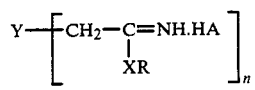

is reacted with a compound of the formula III

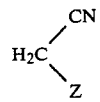

where $A^\ominus$ is an anion.

The compounds prepared according to the invention are useful intermediates, for example for the preparation of diazo components.

6 Claims, No Drawings

PREPARATION OF CYANO-SUBSTITUTED ENOL ETHERS

The present invention relates to a process for the preparation of compounds of the formula I

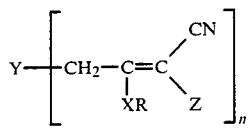

where R is alkyl of 1 to 10, preferably 1 to 4, carbon atoms, X is O or S, Y is hydrogen or nitrophenyl which is unsubstituted or substituted by chlorine, bromine, methoxy or methyl, when n is 1, and is $C_2$-$C_6$-alkylene when n is 2, and Z is cyano or 2-benzimidazolyl, wherein an iminoether of the formula II

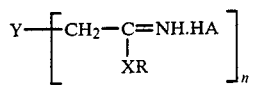

is reacted with a compound of the formula III

where $A^\ominus$ is an anion.

The reaction is preferably carried out in a solvent, such as methanol, ethanol, propanol, acetic acid, dimethylformamide, tetrahydrofuran, chloroform, N-methylpyrrolidone or dioxane, ethanol being preferred. The pH during the reaction should be in the neutral to acidic range. During the reaction, the mixture is preferably heated, for example to 40°–100° C.

The reactants are reacted with one another in stoichiometric amounts, although it is of course also possible to use an excess of a component.

In a very advantageous preparation method, a compound of the formula II is prepared in situ from the corresponding nitrile by reaction with HA in a compound of the formula ROH and then reacted with a compound of the formula III.

The compounds of the formula I are useful intermediates, for example for the preparation of diazo components (cf. for example German Laid-Open Application DOS, Patent Application No. P 35 07 421.3).

Of particular importance is the novel process for the preparation of the compound of the formula

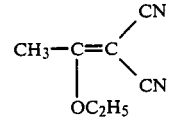

H. Junek and H. W. Schmidt, Monatsh. Chem. 108, (1977), 895 disclose the preparation of this compound starting from the ortho ester of the formula

In comparison, the novel preparation method is very much more advantageous because the expensive synthesis of the ortho ester is dispensed with.

EXAMPLE 1

164 parts of anhydrous sodium acetate are dissolved in 500 parts by volume of acetic acid, 132 parts of malodinitrile and 247 parts of

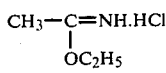

are added, and the mixture is stirred for 2 hours at 60° C.

The reaction mixture is then poured onto 2500 parts of ice water, and the product is filtered off under suction, washed with water and dried to give 207 parts of

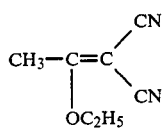

in the form of colorless crystals of melting point 93°–94° C.

The compound is identical to the methylethoxymethylene-malodinitrile obtained by H. W. Schmidt and H. Junek, Monatsh. Chem. 108 (1977), 897, from triethyl orthoacetate and malodinitrile.

EXAMPLE 2

132 parts of malodinitrile and 250 parts of

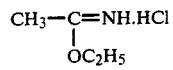

are run into 500 parts by volume of absolute ethanol, the mixture is refluxed for 4 hours and diluted with 2500 parts of ice water, and the product is then filtered off under suction, washed with water and dried to give 235 parts of methylethoxymethylene-malodinitrile.

EXAMPLE 3

200 parts of hydrogen chloride are passed into a mixture of 150 parts by volume of chloroform, 230 parts of absolute ethanol and 205 parts of acetonitrile at 5°–10° C. Stirring is continued overnight at room temperature after which excess hydrogen chloride is removed under reduced pressure. Thereafter, a solution of 264 parts of malodinitrile in 500 parts by volume of absolute ethanol is poured in, and the mixture is heated at the boil under a descending condenser. Chloroform distills off. When an internal temperature of 78° C. is reached, refluxing is continued for a further 4 hours and the reaction mixture is discharged onto 2000 parts of ice water. The product is filtered off under suction, washed with water and dried to give 486 parts of methyethoxymethylene-malodinitrile.

EXAMPLE 4

157 parts os 2-cyanomethylbenzimidazole and 125 parts of

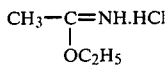

are introduced into 250 parts by volume of acetic acid, and the mixture is stirred for 4 hours at 60° C. The reaction mixture is then poured onto about 1000 parts of ice water and rendered neutral with ammonia. The precipitated product is filtered off under suction, washed with water and dried at 80° C. under reduced pressure. 195 parts of the compound

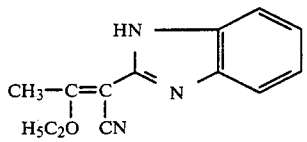

are obtained. A sample recrystallized from pentanol has a melting point of 216°–217° C. and gives the following analytical values:

$C_{13}H_{13}N_3O$ (227): calculated: C 68.8, H 5.7, N 18.5, O 7.0. found: C 68.5, H 5.5, N 18.6, O 7.2.

EXAMPLE 5

66 parts of malodinitrile are dissolved in 500 parts by volume of absolute ethanol, and 244.5 parts of

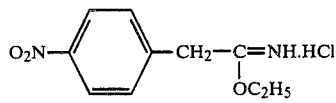

are added. The mixture is refluxed for 6 hours and then poured onto 2000 parts of ice water. The product is filtered off under suction, washed with water and dried to give 211 parts of the compound

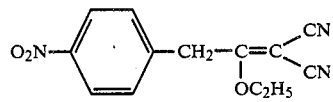

A sample recrystallized from ethanol melts at 106°–107° C. and gives the following analytical values:

$C_{13}H_{11}N_3O_3$ (227): calculated: C 60.7, H 4.3, N 16.3, O 18.7. found: C 60.4, H 4.4, N 16.5, O 19.1.

The following compounds are obtained by the same method:

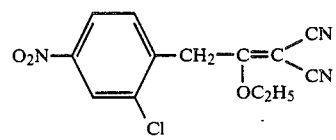

Mp.=169°–170° C. (acetic acid).
calculated: Cl 12.2; found: 12.2%.

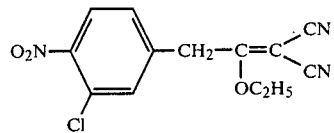

Mp.=94°–95° C. (ethanol).
calculated: Cl 12.2; found: 12.1%.

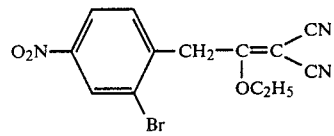

Mp.=186°–187° C. (ethanol).
calculated: Br 23.8; found: 24.4%.

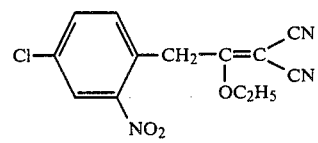

Mp.=114°–115° C. (ethanol).
calculated: Cl 12.2; found: 11.9%.

EXAMPLE 6

157 parts of 2-cyanomethylbenzimidazole are dissolved in 1000 parts by volume of absolute ethanol. 244.5 parts of

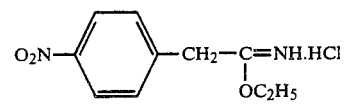

are added, and the mixture is refluxed for 6 hours, cooled and then diluted with 500 parts by volume of water and left to crystallize overnight. The compound is then filtered off under suction, washed with 50% strength ethanol and dried at 80° C. under reduced pressure. 282 parts of

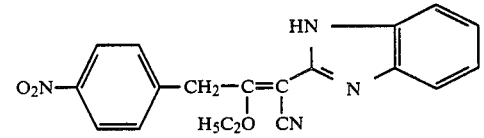

are obtained. A sample recrystallized from dimethylformamide melts at 320° C. with decomposition and gives the following analytical values:

$C_{19}H_{16}N_4O_3$ (348): calculated: C 65.5, H 4.6, N 16.1, O 13.8. found: C 65.7, H 4.9, N 15.8, O 13.5.

EXAMPLE 7

273 parts of $$HN=C-CH_2-CH_2-CH_2-CH_2-C=NH \cdot 2HCl$$
$$\phantom{HN=}|\phantom{-CH_2-CH_2-CH_2-CH_2-}|$$
$$\phantom{HN=}OC_2H_5 \phantom{-CH_2-CH_2-CH_2-CH_2-}OC_2H_5$$

are introduced into a solution of 140 parts of malodinitrile in 500 parts by volume of absolute ethanol, and the mixture is refluxed for 16 hours and then left to cool, after which the stirred solution is diluted with 300 parts of water in the course of 4 hours. The product is filtered off under suction and dried to give 177 parts of the compound $$\underset{NC}{\overset{NC}{>}}C=C-CH_2-CH_2-CH_2-CH_2-C=C\underset{CN}{\overset{CN}{<}}$$
$$\phantom{NC>C=}|\phantom{-CH_2-CH_2-CH_2-CH_2-}|$$
$$\phantom{NC>C=}OC_2H_5 \phantom{-CH_2-CH_2-CH_2-CH_2-}OC_2H_5$$

in the form of colorless crystals of melting point 120°–121° C. (from ethanol).

$C_{16}H_{18}N_4O_2$ (298): calculated: C 64.4, H 6.1, N 18.8, O 10.7. found: C 64.4, H 6.3, N 18.8, O 10.9.

EXAMPLE 8

82 parts of anhydrous sodium acetate are dissolved in 500 parts of acetic acid. 66 parts of malodinitrile and 202 parts of $$CH_3-C=NH \cdot HCl$$
$$\phantom{CH_3-}|$$
$$\phantom{CH_3-}SCH_2C_6H_5$$

are added, and the mixture is stirred for 2 hours at 60° C. The mixture is then introduced into 1000 parts of ice water, and the product is filtered off under suction, washed with water and dried to give 142 parts of $$CH_3-C=C\underset{CN}{\overset{CN}{<}}$$
$$\phantom{CH_3-}|$$
$$\phantom{CH_3-}SCH_2C_6H_5$$

A sample recrystallized from toluene melts at 102°–103° C. and gives the following analytical values:

$C_{12}H_{10}N_2S$ (214): calculated: C 67.3, H 4.7, N 13.1, S 15.0. found: C 67.2, H 4.8, N 13.1, S 14.7.

I claim:

1. A process for the preparation of a compound of the formula I $$Y-\left[CH_2-C=C\underset{Z}{\overset{CN}{<}}\right]_n$$
$$\phantom{Y-[CH_2-}|$$
$$\phantom{Y-[CH_2-}XR$$

where R is alkyl of 1 to 10 carbon atoms, X is O or S, n is 1 or 2, Y is hydrogen or nitrophenyl which is unsubstituted or substituted by chlorine, bromine, methoxy or methyl when n is 1 and is $C_2$-$C_6$-alkylene when n is 2, and Z is cyano or 2-benzimidazolyl, wherein an iminoether of the formula II $$Y-\left[CH_2-C=NH \cdot HA\right]_n$$
$$\phantom{Y-[CH_2-}|$$
$$\phantom{Y-[CH_2-}XR$$

is reacted with a compound of the formula III $$H_2C\underset{Z}{\overset{CN}{<}}$$

where $A^\ominus$ is an anion and R, X, Y, n and Z have the above meanings.

2. A process as claimed in claim 1, wherein R is $C_2H_5$.
3. A process as claimed in claim 1, wherein X is O.
4. A process as claimed in claim 1, wherein the compound of the formula $$CH_3-C=C\underset{CN}{\overset{CN}{<}}$$
$$\phantom{CH_3-}|$$
$$\phantom{CH_3-}OC_2H_5$$

is prepared from the compounds $$CH_3-C=NH \cdot HA$$
$$\phantom{CH_3-}|$$
$$\phantom{CH_3-}OC_2H_5$$

and $CH_2(CN)_2$, where HA is HCl or other strong acid.

5. A process as claimed in claim 1, wherein the reaction is carried out at 40° to 100° C. in a solvent at neutral or acidic pH.

6. A process as claimed in claim 1, wherein the compound of the formula II is prepared in situ from the corresponding nitrile by reaction with HA in a compound of the formula RXH.

* * * * *